(12) United States Patent
Oberkofler et al.

(10) Patent No.: US 11,427,862 B2
(45) Date of Patent: Aug. 30, 2022

(54) OLIGONUCLEOTIDES AND METHODS FOR INTERNAL CONTROL OF EUKARYOTIC DNA AMPLIFICATION REACTIONS

(71) Applicant: CENTRO DI SPERIMENTAZIONE LAIMBURG, Vadena (IT)

(72) Inventors: Vicky Oberkofler, Andriano (IT); Katrin Janik, Bolzano (IT)

(73) Assignee: CENTRO DI SPERIMENTAZIONE LAIMBURG, Vadena (IT)

( * ) Notice: Subject to any disclaimer, the term of this patent is extended or adjusted under 35 U.S.C. 154(b) by 58 days.

(21) Appl. No.: 16/978,910

(22) PCT Filed: Mar. 6, 2019

(86) PCT No.: PCT/EP2019/055506
§ 371 (c)(1),
(2) Date: Sep. 8, 2020

(87) PCT Pub. No.: WO2019/170709
PCT Pub. Date: Sep. 12, 2019

(65) Prior Publication Data
US 2021/0024986 A1     Jan. 28, 2021

(30) Foreign Application Priority Data
Mar. 6, 2018 (IT) .................. 102018000003299

(51) Int. Cl.
*C12Q 1/68* (2018.01)
*C12Q 1/6844* (2018.01)
*C12Q 1/6888* (2018.01)

(52) U.S. Cl.
CPC ......... *C12Q 1/6844* (2013.01); *C12Q 1/6888* (2013.01); *C12Q 2545/101* (2013.01)

(58) Field of Classification Search
CPC ..................................................... C12Q 1/68
USPC ........................................................ 435/6.12
See application file for complete search history.

(56) References Cited

FOREIGN PATENT DOCUMENTS

| CN | 105154576 A | 12/2015 | | |
|----|----|----|----|----|
| WO | 2005003384 A1 | 1/2005 | | |
| WO | WO-2005003384 A1 * | 1/2005 | ........... | C12Q 1/6848 |
| WO | 2006048291 A2 | 5/2006 | | |

OTHER PUBLICATIONS

Applied Biosystems, "Eukaryotic 18S rRNA Endogenous Control (FAM™/MGB probe, non-primer limited)" Catalog No. 4333760F, pp. 1-4.
Birte Vester et al., LNA (Locked Nucleic Acid): High-Affinity Targeting of Complementary RNA and DNA, Biochemistry, Oct. 2, 2004, vol. 43, No. 42, Abstract (pp. 13233-13241).
C. H. Dietrich et al., "Phylogeny of the Major Lineages of Membracoidea (Insecta: Hemiptera: Cicadomorpha) Based on 28S rDNA Sequences", Molecular Phylogenetics and Evolution, 2001, vol. 18, No. 2, Abstract.
G. Piorkowski et al., "Development of generic Taqman PCR and RT-PCR assays for the detection of DNA and mRNA of beta-actin-encoding sequences in a wide range of animal species", Journal of virological methods, 2014, vol. 202, Abstract (pp. 101-105).
International Search Report dated May 13, 2019 re: Application No. PCT/EP2019/055506, pp. 1-5, citing: CN 105 154 576 A, WO 2005/003384 A1, WO 2006/048291 A2, Subbotin et al. "A rapid method . . . " and Sharma et al. "Diffentiation of Members . . . ".
Isabelle Meusier et al., "A universal DNA mini-barcode for biodiversity analysis", BMC Genomics, May 12, 2008, vol. 9, No. 1, pp. 214-217.
IT Search Report dated Oct. 25, 2018 re: Application No. IT 2018000003299, pp. 1-11, citing: CN 105 154 576 A, WO 2005/003384 A1, WO 2006/048291 A2, Subbotin et al. "A rapid method . . . " and Sharma et al. "Differentiation of members . . . ".
Kenan Hadziavdic et al. "Characterization of the 18S rRNA Gene for Designing Universal Eukaryote Specific Primers", PLOS One, 2014, vol. 9, No. 2.
L.E. Blankenship et al., "Universal primers and PCR of gut contents to study marine invertebrate diets", Molecular Ecology, 2005, vol. 14, No. 3, 891-899.
M. Monti et al., "EvaGreen Real-time PCR protocol for specific 'Candidatus Phytoplasma mali' detection and quantification in insects", Mol Cell Probes, 2013, vol. 27, No. 3-4, pp. 129-136.
Mikael Kubista, et al., "The real-time polymerase chain reaction", Molecular Aspects of Medicine, 2006, vol. 27, No. 2, Abstract (pp. 95-125).
O.P. Singh et al. "Differentiation of Members of the *Anopheles Fluviatilis* Species Complex by an Allele-Specific Polymerase Chain Reaction Based on 28S Ribosomal DNA Sequences", American Journal of Tropical Medicine & Hygiene, Jan. 1, 2004, vol. 701, No. 1, pp. 27-32, XP055518756.
Raul Rivas et al., "Identification of microorganisms by PCR amplification and sequencing of a universal amplified ribosomal region present in both prokaryotes and eukaryotes" Journal of Microbiological Methods, Mar. 2004, vol. 56, No. 3, pp. 413-426.
Sergei A. Subbotin et al. "A rapid method for the identification of the soybean cyst nematode Heterodera Glycines using duplex PCR", Nematology, 2001, vol. 3, No. 4, pp. 365-371, XP009090397.
Written Opinion dated May 13, 2019 re: Application No. PCT/EP2019/055506, pp. 1-7, citing: CN 105 154 576 A, WO 2005/003384 A1, WO 2006/048291 A2, Subbotin et al. "A rapid method . . . " and Sharma et al. "Diffentiation of Members . . . ".

(Continued)

*Primary Examiner* — Aaron A Priest
(74) *Attorney, Agent, or Firm* — Cantor Colburn LLP

(57) ABSTRACT

Oligonucleotides may be universal primers and probes. Method may use these oligonucleotides for detecting or detecting and quantifying a nucleic acid acting as a universal internal control. A primer pair includes a first primer having SEQ ID NO: 1 or a complement thereof and a second primer having SEQ ID NO: 2 or a complement thereof. A probe includes SEQ ID NO: 3 or a complement thereof, preferably wherein each of the nucleotides in position 4, 5, 6, 8, 9, 10, 11 and 12 of SEQ ID NO: 3 is replaced with a corresponding locked nucleic acid (LNA) unit (SEQ ID NO: 4).

6 Claims, No Drawings
Specification includes a Sequence Listing.

(56) References Cited

OTHER PUBLICATIONS

Yong Wang et al., "Optimal Eukaryotic 18S and Universal 16S/18S Ribosomal RNA Primers and Their Application in a Study of Symbiosis", PLOS One, 2014, vol. 9, No. 3, pp. 1-11.

* cited by examiner

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Ciq_qPCR fwd - 28S Forward primer
```

-continued

```
<400> SEQUENCE: 1
ctactatcta gcgaaacc                                                  18

<210> SEQ ID NO 2
<211> LENGTH: 18
<212> TYPE: DNA
<213> ORGANISM: Artificial Sequence
<220> FEATURE:
<223> OTHER INFORMATION: Ciq_qPCR_2_rev - 28S Reverse primer

<400> SEQUENCE: 2
aytagagtca agctcaac                                                  18

<210> SEQ ID NO 3
<211> LENGTH: 12
<212> TYPE: DNA
<213> ORGANISM: Artificial Sequence
<220> FEATURE:
<223> OTHER INFORMATION: 28S probe

<400> SEQUENCE: 3
aaagaagacc ct                                                        12

<210> SEQ ID NO 4
<211> LENGTH: 12
<212> TYPE: DNA
<213> ORGANISM: Artificial Sequence
<220> FEATURE:
<223> OTHER INFORMATION: Insect.p - 28S probe
<220> FEATURE:
<221> NAME/KEY: misc_feature
<222> LOCATION: (4)..(6)
<223> OTHER INFORMATION: LNA units with 2'-O,4'-C-methylene bridged
      sugar
<220> FEATURE:
<221> NAME/KEY: misc_feature
<222> LOCATION: (8)..(12)
<223> OTHER INFORMATION: LNA units with 2'-O,4'-C-methylene bridged
      sugar

<400> SEQUENCE: 4
aaagaagacc ct                                                        12

<210> SEQ ID NO 5
<211> LENGTH: 84
<212> TYPE: DNA
<213> ORGANISM: Artificial Sequence
<220> FEATURE:
<223> OTHER INFORMATION: 28S consensus sequence
<220> FEATURE:
<221> NAME/KEY: primer_bind
<222> LOCATION: (1)..(18)
<223> OTHER INFORMATION: Fwd primer binding region
<220> FEATURE:
<221> NAME/KEY: misc_binding
<222> LOCATION: (55)..(66)
<223> OTHER INFORMATION: Probe binding region
<220> FEATURE:
<221> NAME/KEY: primer_bind
<222> LOCATION: (67)..(84)
<223> OTHER INFORMATION: Rev primer binding region

<400> SEQUENCE: 5
ctactatcta gcgaaaccac wgccarggga acggkcytgg aaaaatyagy ggggaaagaa    60
gaccctgttg agcttgactc tart                                           84
```

OLIGONUCLEOTIDES AND METHODS FOR INTERNAL CONTROL OF EUKARYOTIC DNA AMPLIFICATION REACTIONS

TECHNICAL FIELD

The present disclosure generally relates to the field of nucleic acids amplification and more particularly to methods involving the amplification and the detection/quantification of a universal control nucleotide sequence, and to primers, probes and kits useful in such methods.

BACKGROUND

The reliable detection of nucleic acids plays an important role in different applications in many research fields, especially in molecular diagnostics. Internal controls to assess nucleic acids integrity and the absence of PCR inhibitors in amplification reactions are indispensable tools for molecular pathogen detection and gene expression studies. These studies are usually based on the detection of a specific target nucleic acid (e.g. a gene or DNA fragment from a pathogen or an expressed gene) and the parallel (i.e. in different reaction vessels) or multiplex (i.e. in the same reaction vessel) detection of an internal control (a gene, RNA or DNA fragment from the host) that proves the overall presence and integrity of the nucleic acids and the absence of PCR inhibitors in the respective sample.

Molecular pathogen detection assays are used also for phytoplasmas detection. Phytoplasmas are plant pathogens responsible for severe disorders in both ornamental plants and fruit crops. In particular, *Candidatus* Phytoplasma mali is the causal agent of apple proliferation disease, a serious disorder that affects apple trees and causes significant economic losses to apple growers.

The infection cycle of the *Candidatus* Phytoplasma mali-caused disease involves multitrophic interactions between the pathogen and different hosts, i.e. insects and plants. In fact, phytoplasmas are bacterial pathogens which require a host plant as a reservoir of the disease and an insect host that contributes to spreading the pathogen from an infected plant to a healthy one.

The main insect vectors responsible for spreading the *Candidatus* Phytoplasma mali-caused disease are two psyllids, *Cacopsylla picta* and *Cacopsylla melanoneura*. The disease may also be transmitted by means of the conventional plant multiplication techniques, such as grafting, when using infected propagating material and, to a lesser extent, by the formation of root anastomoses between diseased plants and adjacent healthy plants. Accordingly, studying and monitoring of the *Candidatus* Phytoplasma mali-caused disease requires the ability to reliably detect the pathogen in different insect species and plants.

The sequences of primers and probes for the detection of *Candidatus* Phytoplasma mali have been published (Ref 1). However, in the literature there are no reports of suitable universal primers for an internal control which is useful for the reliable detection of the pathogen's DNA in samples obtained from a variety of eukaryotic organisms.

Most published internal controls for quantitative PCR are species-specific or are very narrow regarding detection in different species. This causes limitations for the detection system, since the specificity of the internal control determines in which organisms the target nucleic acid can be reliably detected. Several publications address the design of universal primers for different purposes, but mainly for amplifying long stretches of DNA for phylogenetic analyses (Refs. 3-8) and not as a universal internal control for quantitative PCR analysis. In particular, quantitative real-time PCR (Ref 11) requires primers generating relatively short amplification products, preferably no longer than about 100 bp.

A commercially available primer/probe set, based on the eukaryotic 18S rRNA gene, for use as a universal internal control is marketed by Applied Biosystems™ and consists of a ready to use primer/probe mix for amplifying a stretch on the 18S rRNA gene (Ref 2). However, the sequences of this primer/probe set are not available and their use is always coupled to purchasing the primer/probe set from the manufacturer at the given price.

The β-actin gene was considered as a potential universal control in DNA and RNA detection (Ref 9), but an in silico analysis revealed that the β-actin sequence of several insect species is not sufficiently conserved to be a suitable universal control in assays where the sample is obtained from those insect species.

To our knowledge, no publication provides sequence information for a universal primer/probe set applicable as a reliable internal control for the quantitative PCR detection of a target nucleic acid in a vast set of eukaryotic organisms, ranging from yeast cells to humans.

SUMMARY

In view of the above, the aim of the present disclosure is to provide a universal control for amplification reactions which is reliably amplified across a vast set of eukaryotic organisms.

The present disclosure provides a universal control which is cost effective and allows to verify sample integrity and absence of PCR inhibitors, particularly for validating negative diagnostic results.

The present disclosure provides a control that can be used to verify sample integrity and absence of PCR inhibitors in both qualitative and quantitative molecular assays targeting DNA or RNA.

The disclosure further provides means for verifying sample integrity and absence of PCR inhibitors in single- or multiplex detection assays and in assays where multiple targets are detected and/or quantified in parallel.

The aim, as well as these and other advantages which will become better apparent hereinafter, are achieved by providing a primer pair consisting of a first primer comprising SEQ ID NO: 1 or a complement thereof and a second primer comprising SEQ ID NO: 2 or a complement thereof.

The aim and advantages of the present disclosure are also achieved by providing a probe comprising SEQ ID NO: 3 or a complement thereof.

Moreover, the aim and advantages of the disclosure are achieved by providing a composition comprising the primer pair and optionally the probe described above.

The aim and advantage of the disclosure are achieved also by providing a kit comprising:
 (a) the primer pair of the disclosure; and
 (b) optionally the probe of the disclosure.

The aim and advantage of the disclosure are achieved also by providing an internally controlled method of amplification of nucleic acids in a test sample, wherein the test sample comprises a control sequence comprising SEQ ID NO: 5 and the method comprises:
 (a) forming a mixture by contacting the test sample with the primer pair of the disclosure;

(b) subjecting the mixture formed in (a) to a nucleic acid amplification under conditions to generate an amplification product of the control sequence; and (c) detecting the presence and/or quantifying the amount of the control sequence.

Finally, the aim and advantage of the disclosure are achieved also by providing an internally controlled method of amplification of nucleic acids in a test sample, wherein the test sample comprises a control sequence comprising SEQ ID NO: 5 and potentially comprises one or more target sequences and the method comprises:

(a) forming a mixture by contacting the sample with the primer pair of the disclosure;

(b) forming one or more mixtures contacting the test sample with at least one primer pair specific for the one or more target sequences;

(c) subjecting the one more mixtures formed in (a) and (b) to a nucleic acid amplification under conditions to generate amplification products of the control sequence and of the one or more target sequences; and (d) detecting the presence and/or quantifying the amount of the control sequence.

DETAILED DESCRIPTION OF THE DISCLOSURE

Further characteristics and advantages of the disclosure will become better apparent from the following detailed description of the disclosure.

Throughout the description and claims the following definitions shall apply.

The terms "target sequence", "target nucleic acid" and "target nucleic acid sequence" are synonymous and are used herein to denote a nucleic acid in a test sample which should be analyzed, i.e. the presence, non-presence and/or amount thereof in a sample should be determined.

The terms "control sequence" or "nucleic acid control" as used herein refer to a nucleic acid based on the eukaryotic 28S rRNA gene comprising, or consisting essentially of, or consisting of a sequence of SEQ ID NO: 5 and which serves as a universal internal control, i.e. the amplification and/or amount of which are determined to assess nucleic acids integrity and the absence of amplification inhibitors in the test sample.

The terms "test sample" or "sample" refer to a material obtained from a eukaryotic organism, such as yeast cells, fungi, plants, arthropods including insects and arachnids, fishes, or mammals including humans, that is suspected of containing or potentially contains at least one target nucleic acid of interest and contains the control sequence. The test sample can be pre-treated prior to use in the methods of the present disclosure by, for example, preparing plasma or serum from blood, disrupting cells, preparing liquids from solid materials, diluting viscous fluids, filtering liquids, distilling liquids, concentrating liquids, inactivating interfering components, adding reagents, purifying nucleic acids, and the like.

The term "reaction vessel" comprises, but is not limited to, tubes or the wells of plates such as microwell, deepwell or other types of multiwell plates, in which the amplification reaction for the analysis of the test sample takes place. Such vessels are made with chemically inert materials, such that they do not interfere with the analytical reaction taking place within.

An "amplification reaction" refers to any chemical, including enzymatic, reaction that results in increased copies of a nucleic acid sequence. A method of nucleic acid amplification is the Polymerase Chain Reaction (PCR) which is well known to the skilled person, and disclosed for example in U.S. Pat. No. 4,683,202. Other amplification reactions comprise, among others, the Ligase Chain Reaction (LCR), Polymerase Ligase Chain Reaction (PLCR), Gap-LCR, Repair Chain Reaction, Strand Displacement Amplification (SDA), Transcription Mediated Amplification (TMA), nucleic acid sequence-based amplification (NASBA), rolling circle amplification (RCA) and loop-mediated isothermal amplification (LAMP).

The term "amplification reagents" refers to chemical or biochemical components that enable the amplification of nucleic acids. Such reagents comprise, but are not limited to, an agent for polymerization (such as a DNA polymerase or reverse transcriptase enzyme), buffers, mononucleotides such as nucleoside triphosphates, oligonucleotides e.g. primers, salts and their respective solutions, detection probes, fluorescent dyes, and more. The composition of the amplification reagents can be appropriately determined by persons skilled in the art depending on the nucleic acids amplification reaction used.

The terms "nucleic acid" or "nucleic acid sequence" or "nucleotide sequence" refer to a deoxyribonucleotide or ribonucleotide polymer (respectively DNA or RNA) in either single- or double-stranded form, including also cDNA. Unless otherwise limited, nucleic acids may encompass known analogues of natural nucleotides that can function in a manner identical to or similarly to naturally occurring nucleotides.

The terms "corresponding nucleotide analogue" and "corresponding nucleotide" are intended to indicate that the nucleobase in the nucleotide analogue and that in the nucleotide are identical. For example, when a nucleotide contains adenine as its nucleobase, then the corresponding nucleotide analogue also contains adenine.

A sequence which is the "complement" of or is "complementary" to a specific nucleotide sequence means a sequence capable of base pairing with the specific nucleotide sequence according to the standard Watson-Crick complementarity rules. Specifically, purine bases will base pair with pyrimidine bases to form a combination of guanine paired with cytosine (G:C) and adenine paired with thymine (A:T) in the case of DNA or adenine paired with uracil (A:U) in the case of RNA.

The term "oligonucleotide" refers to a molecule comprised of two or more deoxyribonucleotides or ribonucleotides, such as primers, probes, nucleic acid fragments to be detected, and nucleic acid controls. Oligonucleotides can be prepared by any suitable method known in the art, including for example, cloning and restriction of appropriate sequences and direct chemical synthesis, such as the conventional and well-known phosphoramidite chemistry. In the context of the present disclosure, oligonucleotides may be chemically modified, i.e. the primer and/or the probe may comprise one or more modified nucleotides or non-nucleotide compounds.

The term "primer" is used herein as known to the skilled person and refers to natural or synthetic oligonucleotides capable of acting as a point of initiation of DNA synthesis under conditions in which synthesis of a primer extension product complementary to a nucleic acid strand is induced, i.e. in the presence of four different nucleoside triphosphates and an agent for polymerization (such as a DNA polymerase or reverse transcriptase enzyme) in an appropriate buffer and at a suitable temperature.

The term "probe" refers to a natural or synthetic oligonucleotide capable of hybridizing under suitable conditions to an amplification product of a nucleic acid for the purpose of detecting that amplification product. For this purpose, probes typically carry labels (e.g. a fluorophore and/or a fluorescence quencher). Labeled probes include, among others, molecular beacon probes, TaqMan® probes, Scorpion probes, TaqMan® MGB probes and others known to the skilled person. It is well understood that the term probe encompasses also unlabeled oligonucleotides used, for example, in association with intercalating agents in detection systems based on melting analysis, such as High Resolution Melting (HRM).

The term "label" as used herein refers generally to a molecular moiety that makes a nucleic acid distinguishable. For example, labels include fluorophores and quenchers.

As used herein, the term "fluorophore" refers generally to a molecular moiety that emits light when it is excited by light of another wavelength. Exemplary fluorophores include, but are not limited to fluorescein dyes such as 5-carboxyfluorescein (5-FAM), 6-carboxyfluorescein (6-FAM), hexachlorofluorescein (HEX), tetrachlorofluorescein (TET™) and 6-carboxy-4',5'-dichloro-2',7'-dimethoxyfluorescein (JOE); rhodamine dyes such as Rhodamine, Rhodamine B, Rhodamine 6G, tetramethylrhodamine (TAMRA™) and rhodamine isothiocyanate; cyanine dyes such as Cy3™ Cy3.5™, Cy5™, Cy5.5™ and Cy7™; LightCycler® (LC) dyes such as LC-Yellow 555, LC-Red 610, LC-Red 640, LC-Red 670 and LC-Red 705; and Alexa Fluor® dyes such as Alexa 488, Alexa 546 and Alexa 647.

The term "quencher" refers generally to a molecular moiety that can efficiently decrease the intensity of the fluorescence emitted by a fluorophore. A quencher may be a fluorophore or a molecular structure not emitting visible light, such as Dabcyl (N-[4-(4-dimethylamino)phenylazo] benzoic acid), a Black Hole Quencher® that quenches across the entire visible spectrum, an IRDye® QC-1 quencher, a QXL® quencher, an Iowa Black® FQ quencher that quenches in the green-yellow part of the spectrum, or an Iowa Black® RQ quencher that quenches in the orange-red part of the spectrum.

The present disclosure provides novel oligonucleotides, kits and methods providing a universal internal control system for assessing sample integrity and absence of inhibitors which could potentially affect target detection and quantification in molecular assays on samples obtained from a wide range of eukaryotic organisms, including fungi, plants, arthropods, fishes and mammals.

The design of a universal primer pair and probe was carried out due to the necessity of a universal internal control that allows detection of the plant pathogen *Candidatus* Phytoplasma mali in different host organisms. Based on in silico analysis the present inventors have identified a sequence (SEQ ID NO: 5) of the 28S rRNA gene that is highly conserved across different insect species as well as other eukaryotic organisms.

In a first aspect, the present disclosure refers to a primer pair consisting of a first primer comprising, preferably consisting essentially of, more preferably consisting of SEQ ID NO: 1 or a complement thereof and a second primer comprising, preferably consisting essentially of, more preferably consisting of SEQ ID NO: 2 or a complement thereof.

Most preferably, the two primers comprise, or consist essentially of, or consist of the nucleotide sequences of respectively SEQ ID NO: 1 and SEQ ID NO:2. However, it is appreciated that the complements of the aforementioned primers are equally suitable for use in the present disclosure.

The amplification product generated by primers comprising, preferably consisting essentially of, more preferably consisting of respectively SEQ ID NOs: 1 and 2 is highly conserved across many eukaryotic organisms, such as fungi, plants, arthropods, fishes and mammals. This is an essential requirement for an efficient probe design.

The present disclosure refers also to a probe comprising, preferably consisting essentially of, more preferably consisting of SEQ ID NO: 3 or a complement thereof.

To design a probe with ideal PCR characteristics, such as sensitivity and specificity, one or more nucleotides in the probe may be replaced with corresponding nucleotide analogues. Different nucleotide analogues can be used to achieve the desired base pairing properties. Those include, among others, peptide nucleic acid (PNA), Morpholino, glycol nucleic acid (GNA), threose nucleic acid (TNA), xeno nucleic acid (XNA) and locked nucleic acid (LNA). The use of LNA units is known from e.g. Ref 10.

In a preferred embodiment, one or more nucleotides of SEQ ID NO: 3 are replaced with corresponding nucleotide analogues which are locked nucleic acid (LNA) units.

In a more preferred embodiment, each of the nucleotides in position 4, 5, 6, 8, 9, 10, 11 and 12 of SEQ ID NO: 3 is replaced with a corresponding LNA unit (SEQ ID NO: 4).

Most preferably, the probe comprises, or consists essentially of, or consists of the nucleotide sequence of SEQ ID NO: 3 or SEQ ID NO: 4. However, it is appreciated that the complements of the aforementioned probes are similarly suitable for use in the present disclosure.

In another preferred embodiment the probe is labeled. In particular, the probe may be labeled with one or more labels, such as fluorophores and/or quenchers. In a preferred embodiment, the probe is labeled with both a fluorophore and a quencher.

Fluorophores may be selected from the group consisting of fluorescein dyes such as 5-carboxyfluorescein (5-FAM), 6-carboxyfluorescein (6-FAM), hexachlorofluorescein (HEX), tetrachlorofluorescein (TET™) and 6-carboxy-4',5'-dichloro-2',7'-dimethoxyfluorescein (JOE); rhodamine dyes such as Rhodamine, Rhodamine B, Rhodamine 6G, tetramethylrhodamine (TAMRA™) and rhodamine isothiocyanate; cyanine dyes such as Cy3™ Cy3.5™, Cy5™, Cy5.5™ and Cy7™; LightCycler® (LC) dyes such as LC-Yellow 555, LC-Red 610, LC-Red 640, LC-Red 670 and LC-Red 705; and Alexa Fluor® dyes such as Alexa 488, Alexa 546 and Alexa 647.

Quenchers may be selected from the group consisting of a fluorophore and a molecular structure not emitting visible light, such as Dabcyl (N-[4-(4-dimethylamino)phenylazo] benzoic acid), a Black Hole Quencher®, an IRDye® QC-1 quencher, a QXL® quencher, an Iowa Black® FQ quencher, and an Iowa Black® RQ quencher.

In a more preferred embodiment, the probe is labeled with a fluorophore which is 5'-hexachlorofluorescein (5'-HEX) and a quencher which is 3'-Dabcyl (3'-DAB).

In a most preferred embodiment, the probe consists of SEQ ID NO: 4 and is labeled with 5'-HEX and 3'-DAB.

It will be understood that primers comprising, or consisting essentially of, or consisting of any of the sequences of SEQ ID NOs: 1-2 as well as probes comprising, or consisting essentially of, or consisting of any of the sequences of SEQ ID NOs: 3-4 also encompass oligonucleotides comprising, or consisting essentially of, or consisting of a homologue of any of SEQ ID NOs: 1-4. Homologues are nucleic acids having at least one alteration in the sequence that does not destroy the ability of the primers and probes to hybridize to a stretch of the highly conserved sequence of the 28S rRNA gene (SEQ ID NO: 5). Accordingly, the sequence of any of SEQ ID NOs: 1-4 can be altered, for example, by the insertion, addition, deletion or substitution of one or more nucleotides.

Ordinarily, the homologues will have a nucleic acid sequence having at least about 50%, 60%, 70%, 80%, 85%, 90% or 95% nucleic acid sequence identity with a nucleic acid sequence set forth in any of SEQ ID NOs: 1-4. Identity with respect to such sequences is defined herein as the percentage of nucleotides in the candidate sequence that are identical with the known polynucleotides after aligning the sequences and introducing gaps, if necessary, to achieve the maximum percent identity. Terminal (5' or 3') or internal deletions, extensions or insertions into the nucleotide sequence shall not be construed as affecting identity.

The present disclosure refers also to a primer/probe set consisting of the primer pair and the probe according to any of the embodiments described above.

The present disclosure also refers to a composition comprising the primer pair and optionally the probe according to any of the embodiments described above.

According to another aspect, the disclosure also provides a kit comprising:
(a) the primer pair according to the disclosure; and
(b) optionally the probe according to any of the embodiments described above.

In a preferred embodiment, the kit comprises the primer/probe set consisting of the primer pair according to the disclosure and the probe according to any of the embodiments described above. More preferably, the primer/probe set consists of:
a primer of SEQ ID NO:1;
a primer of SEQ ID NO: 2; and
a probe of SEQ ID NO: 4 labeled with 5'-HEX and 3'-DAB.

According to another aspect, the present disclosure also refers to an internally controlled method of amplification of nucleic acids in a test sample, wherein the test sample comprises a control sequence comprising SEQ ID NO: 5 and the method comprises:
(a) forming a mixture by contacting the test sample with the primer pair of the disclosure;
(b) subjecting the mixture formed in (a) to a nucleic acid amplification under conditions to generate an amplification product of the control sequence; and
(c) detecting the presence and/or quantifying the amount of the control sequence.

The present disclosure also refers to an internally controlled method of amplification of nucleic acids in a test sample, wherein the test sample comprises a control sequence comprising SEQ ID NO: 5 and potentially comprises one or more target sequences and the method comprises:
(a) forming a mixture by contacting the sample with the primer pair according to the disclosure;
(b) forming one or more mixtures contacting the test sample with at least one primer pair specific for the one or more target sequences;
(c) subjecting the one more mixtures formed in (a) and (b) to a nucleic acid amplification under conditions to generate amplification products of the control sequence and of the one or more target sequences; and
(d) detecting the presence and/or quantifying the amount of the control sequence.

In a preferred embodiment of the above methods, the mixture of step (a) further comprises the probe according to the disclosure, the probe forming a hybrid with the amplification product of the control sequence; and the hybrid formed between the probe and the amplification product of the control sequence is detected, whereby the presence of the control sequence is detected and/or the amount of the control sequence is quantified.

In another preferred embodiment of the above methods according to the disclosure, the mixture of step (a) further comprises a nucleic acid intercalating agent. The intercalating agent binds to the amplification product of the control sequence and the amplification product of the control sequence bound to the intercalating agent is detected.

The nucleic acid intercalating agent may be selected, among others, from the group consisting of ethidium bromide, propidium iodide, Sybr® Green, PicoGreen®, EvaGreen®, YO-PRO® and YOYO®.

In yet another embodiment of the above methods according to the disclosure, the mixture of step (a) further comprises a nucleic acid intercalating agent and a probe. The intercalating agent binds to the hybrid formed between the probe and the amplification product of the control sequence, whereby the presence of the control sequence is detected by melting analysis, particularly by high resolution melting (HRM).

In some embodiments of the methods using an intercalating agent, the presence of the control sequence is detected. In some other embodiments, the control sequence is detected and its amount is quantified.

The methods of the disclosure where detection is achieved using intercalating agents and melting analysis allow a cost-effective detection of multiple targets sequences and of the universal control in a single reaction vessel (single-tube) as well as in multiple reaction vessels (parallel). The most suitable assay format (single-tube or multiple tubes) depends on the number and nature of the target sequences of interest. In all assay formats, the universal control and the one or more target sequences are amplified simultaneously.

"Simultaneously", as used herein, means that two or more reactions, such as amplifying a first and a second or more nucleic acids, are performed at the same time and under the same physical conditions.

Accordingly, in one embodiment of the methods of the present disclosure, simultaneous amplification of the at least first and second target nucleic acids is performed in one vessel. In another embodiment of the method, simultaneous amplification is performed with at least one nucleic acid in one vessel and at least a second nucleic acid in a second vessel, at the same time and under the same physical conditions, particularly with respect to temperature and incubation time, and wherein the internal control nucleic acid mentioned above is present in each of said vessels.

The methods according to the disclosure can also be used to provide an internal control for indirect RNA detection assays where the target sequence is an RNA, using nucleic acids amplification assays known to the skilled person.

The methods according to the disclosure can be conveniently used to provide an internal control for assays to detect and/or quantify at least one target nucleic acid in a test sample obtained from a wide range of different eukaryotic organisms, such as fungi, plants, arthropods (including insects and arachnids), fishes and mammals (including humans). For example, the test sample may be obtained from any of the species in the non-limiting list of tested species provided in Table 1 below. In a preferred embodiment, the test sample is obtained from plants or arthropods. In another preferred embodiment, the test sample is suspected of containing or potentially contains at least one target nucleic acid sequence which is a nucleic acid sequence of the plant pathogen *Candidatus* Phytoplasma mali.

It will be understood that the present disclosure also encompasses an isolated polynucleotide comprising, or consisting essentially of, or consisting of a sequence selected from a sequence of SEQ ID NO:5 and a homologue sequence having at least about 50%, 60%, 70%, 80%, 85%, 90% or 95% nucleic acid sequence identity to the sequence set forth in SEQ ID NO: 5, as well as the use of the aforementioned isolated polynucleotide as an internal control in nucleic acid amplification reactions. Of course, the complement of the aforementioned isolated polynucleotide is equally suitable for use in the present disclosure.

The disclosure will now be further described by reference to the following non-limiting example.

EXAMPLE

For the detection of the conserved 28S fragment having SEQ ID NO:5, DNA from the arthropods, fish and mammals listed in Table 1 below was extracted from whole insects or 100 mg of tissue (fish and mammals) using the DNeasy Blood and Tissue Kit (Qiagen), while DNA from the plants and fungi listed in Table 1 below was extracted from 100 mg plant and fungi tissue (leaves, roots or fruiting bodies) using the DNeasy Plant Mini Kit (Qiagen), in line with manufacturer's instructions.

The following PCR conditions were applied for the amplification of the 28S fragment having SEQ ID NO: 5 in a total reaction volume of 10 μL, using 2 μL of template DNA, 5 μL of 2×iQ™ Multiplex Powermix (Biorad), 400 nM of each primer (28S_Fwd_Primer, 5'-CTACTATCTAGCGAAACC-3', SEQ ID NO: 1; 28S_Rev_Primer, 5'-AYTAGAGT-CAAGCTCAAC-3', SEQ ID NO: 2) and 200 nM of the probe (28S_probe, 5'-AAA+G+A+AG+A+C+C+C+T-3' where "+" indicates that the subsequent base is a locked nucleotide (LNA), SEQ ID NO: 4) labeled with 5'-HEX and 3'-DAB. The primers and the probe were custom synthesized using conventional oligonucleotide synthesis chemistry. All PCR analyses were run on a CFX384 Touch Real-Time PCR Detection System (Biorad) applying the following conditions: initial denaturation at 95° C. for 3 minutes, 35 cycles of 95° C. for 15 seconds and 60° C. for 1 minute.

The results of the experiment, expressed in terms of cycle of quantification ($C_q$), i.e. cycle of threshold ($C_T$), values for 28S amplification (defined as the cycle number at which the fluorescent signal crosses the threshold line and can be detected), are summarized in Table 1 below and show that the 28S fragment having SEQ ID NO:5 was detected in all the tested species.

Conversely, when *Escherichia coli* DNA was used in a similarly designed experiment to test amplification of the 28S fragment having SEQ ID NO: 5 in a model prokaryotic organism, the primer/probe set of the present disclosure did not allow amplification and detection of an amplicon of the *Escherichia coli* DNA template.

TABLE 1

| Species | Taxon | Cq value |
|---|---|---|
| Anaceratagallia ribauti | arthropod | 20.17 |
| Aphrophora alni | arthropod | 17.97 |
| Asymmetrasca decedens | arthropod | 16.03 |
| Cacopsylla melanoneura | arthropod | 16.73 |
| Cacopsylla picta | arthropod | 16.24 |
| Cicadula quadrinotata | arthropod | 21.41 |
| Cixius nervosus | arthropod | 10.01 |
| Dicranotropis hamata | arthropod | 13.18 |
| Edwardsiana rosae | arthropod | 14.47 |
| Emelyanoviana mollicula | arthropod | 15.95 |
| Empoasca vitis | arthropod | 22.65 |
| Eriosoma lanigerum | arthropod | 18.02 |
| Ixodida | arthropod | 21.54 |
| Laodelphax striatella | arthropod | 19.51 |
| Macrosteles quadripunctulatus | arthropod | 20.65 |
| Macrosteles cristatus | arthropod | 14.81 |
| Macrosteles laevis | arthropod | 14.62 |
| Macrosteles ossiannilssoni | arthropod | 17.37 |
| Macrosteles sexnotatus | arthropod | 18.96 |
| Psammotettix alienus | arthropod | 17.96 |
| Psammotettix confinis | arthropod | 18.24 |
| Stictocephala bisonia | arthropod | 19.58 |
| Zygina flammigera | arthropod | 18.67 |
| Zyginidia pullula | arthropod | 19.98 |
| Salmo salar | fish | 20.69 |
| Boletus edulis | fungi | 15.42 |
| Saccharomyces cerevisiae | fungi | 17.97 |
| Bos primigenius taurus | mammal | 25.08 |
| Capreolus capreolus | mammal | 22.57 |
| Equus ferus caballus | mammal | 22.95 |
| Homo sapiens | mammal | 26.57 |
| Mus musculus | mammal | 24.09 |
| Ovis gmelini aries | mammal | 22.19 |
| Sus scrofa | mammal | 23.66 |
| Ginkgo biloba | plant | 19.89 |
| Lycopersicon esculentum | plant | 15.4 |
| Malus × domestica | plant | 20.73 |
| Nicotiana occidentalis | plant | 16.95 |
| Olea europaea | plant | 20.28 |
| Pinus cembra | plant | 17.68 |
| Prunus armeniaca | plant | 16.25 |
| Pyrus communis | plant | 20.72 |
| Vitis vinifera | plant | 18.04 |

In practice it has been found that the oligonucleotides and methods according to the disclosure fully achieve the intended aim and advantages, since they provide a cost-effective and reliable solution for verifying sample integrity and absence of inhibitors in nucleic acids amplification reactions performed on samples obtained from a wide range of eukaryotic organisms.

The disclosures in Italian Patent Application No. 102018000003299 from which this application claims priority are incorporated herein by reference.

The invention claimed is:

1. A probe consisting of SEQ ID NO: 3 or a complement thereof, wherein each of the nucleotides in position 4, 5, 6, 8, 9, 10, 11 and 12 of SEQ ID NO: 3 is replaced with a corresponding locked nucleic acid (LNA) unit (SEQ ID NO: 4).

2. The probe according to claim 1 wherein the probe is labeled.

3. A composition comprising a primer pair consisting of a first primer comprising SEQ ID NO: 1 or a complement thereof and a second primer comprising SEQ ID NO: 2 or a complement thereof and the probe according to claim 1.

4. A kit comprising:
    (a) a primer pair consisting of a first primer comprising SEQ ID NO: 1 or a complement thereof and a second primer comprising SEQ ID NO: 2 or a complement thereof; and
    (b) the probe according to claim 1.

5. An internally controlled method of amplification of nucleic acids in a test sample, wherein the test sample comprises a control sequence comprising SEQ ID NO: 5 and wherein the method comprises:
    (a) forming a mixture by contacting the test sample with a primer pair consisting of a first primer comprising SEQ ID NO: 1 or a complement thereof a second primer comprising SEQ ID NO: 2 or a complement thereof;
    (b) subjecting the mixture formed in (a) to a nucleic acid amplification under conditions to generate an amplification product of the control sequence; and
    (c) detecting the presence and/or quantifying the amount of the control sequence,
    wherein the mixture formed in (a) further comprises the probe according to claim 1, the probe forming a hybrid with the amplification product of the control sequence; and
    the hybrid formed between the probe and the amplification product of the control sequence is detected, whereby the presence of the control sequence is detected and/or the amount of the control sequence is quantified.

6. An internally controlled method of amplification of nucleic acids in a test sample, wherein the test sample comprises a control sequence comprising SEQ ID NO: 5 and potentially comprises one or more target sequences and wherein the method comprises:
    (a) forming a mixture by contacting the sample with a primer pair consisting of a first primer comprising SEQ ID NO: 1 or a complement thereof and a second primer comprising SEQ ID NO: 2 or a complement thereof;
    (b) forming one or more mixtures contacting the test sample with at least one primer pair specific for the one or more target sequences;
    (c) subjecting the mixtures formed in (a) and (b) to a nucleic acid amplification under conditions to generate amplification products of the control sequence and of the one or more target sequences; and
    (d) detecting the presence and/or quantifying the amount of the control sequence,
    wherein the mixture formed in (a) further comprises the probe according to claim 1, the probe forming a hybrid with the amplification product of the control sequence; and
    the hybrid formed between the probe and the amplification product of the control sequence is detected, whereby the presence of the control sequence is detected and/or the amount of the control sequence is quantified.

* * * * *